US011666337B2

(12) United States Patent
Baril et al.

(10) Patent No.: US 11,666,337 B2
(45) Date of Patent: Jun. 6, 2023

(54) PURSE STRING SUTURE INSTRUMENT

(71) Applicant: Covidien LP, Mansfield, MA (US)

(72) Inventors: Jacob C. Baril, Norwalk, CT (US);
Garrett P. Ebersole, Hamden, CT (US); Saumya Banerjee, Hamden, CT (US); Justin Thomas, New Haven, CT (US); Matthew A. Dinino, Newington, CT (US); Roy J. Pilletere, Middletown, CT (US)

(73) Assignee: Covidien LP, Mansfield, MA (US)

( * ) Notice: Subject to any disclaimer, the term of this patent is extended or adjusted under 35 U.S.C. 154(b) by 120 days.

(21) Appl. No.: 16/923,850

(22) Filed: Jul. 8, 2020

(65) Prior Publication Data
US 2022/0008072 A1  Jan. 13, 2022

(51) Int. Cl.
*A61B 17/11* (2006.01)
*A61B 17/04* (2006.01)
(Continued)

(52) U.S. Cl.
CPC .......... *A61B 17/11* (2013.01); *A61B 17/0469* (2013.01); *A61B 17/28* (2013.01);
(Continued)

(58) Field of Classification Search
CPC ................ A61B 17/11; A61B 17/0469; A61B 2017/1142; A61B 17/282;
(Continued)

(56) References Cited

U.S. PATENT DOCUMENTS 4,226,241 A * 10/1980 Walker, Jr. ........... A61B 17/282
606/119
4,345,600 A * 8/1982 Rothfuss ............. A61B 17/1114
606/167
(Continued)

FOREIGN PATENT DOCUMENTS

| CN | 109431563 A | 3/2019 |
| CN | 209734062 U | 12/2019 |
| WO | 2004093943 A2 | 11/2004 |

OTHER PUBLICATIONS

Extended European Search dated Nov. 3, 2021 issued in corresponding EP Appln. No. 21183279.5.

*Primary Examiner* — Jing Rui Ou
(74) *Attorney, Agent, or Firm* — Carter, DeLuca & Farrell LLP

(57) ABSTRACT

A purse string suture instrument includes an end effector with first and second jaws disposed at a distal portion of an elongate tubular shaft. The first and second jaws are pivotably coupled to each other and to the elongate tubular shaft. The first and second jaws are spaced apart and define a gap therebetween. First and second pluralities of teeth extend perpendicularly from the first and second jaws respectively, and the first plurality of teeth is longitudinally offset from the second plurality of teeth. The first and second jaws are transitionable between open and approximated configurations. The approximated configuration is adapted to clamp tissue in the gap between the first and second jaws, thereby displacing sections of tissue outwardly between the first and second pluralities of teeth.

12 Claims, 8 Drawing Sheets

(51) Int. Cl.
  *A61B 17/28* (2006.01)
  *A61B 17/29* (2006.01)
(52) U.S. Cl.
  CPC ......... *A61B 17/282* (2013.01); *A61B 17/2812* (2013.01); *A61B 17/2816* (2013.01); *A61B 2017/1142* (2013.01); *A61B 2017/2926* (2013.01); *A61B 2017/2936* (2013.01)
(58) Field of Classification Search
  CPC ........ A61B 2017/2926; A61B 17/2816; A61B 17/2812; A61B 17/28; A61B 2017/2936
  See application file for complete search history.

(56) References Cited

U.S. PATENT DOCUMENTS

| | | | |
|---|---|---|---|
| 4,611,592 A | | 9/1986 | Talboy |
| 5,411,481 A | * | 5/1995 | Allen ................ A61B 17/0469 |
| | | | 606/208 |
| 5,454,822 A | * | 10/1995 | Schob ................ A61B 17/0469 |
| | | | 606/167 |
| 5,649,938 A | | 7/1997 | Allen et al. |
| 6,607,227 B1 | * | 8/2003 | Morton ................ H01R 43/20 |
| | | | 294/119.1 |
| 6,945,444 B2 | | 9/2005 | Gresham et al. |
| 10,448,963 B2 | | 10/2019 | Crockett et al. |
| 10,646,217 B2 | * | 5/2020 | Pisarnwongs ...... A61B 17/0482 |
| 2009/0275902 A1 | * | 11/2009 | Heeps ................ A61B 17/1285 |
| | | | 606/151 |
| 2009/0312602 A1 | | 12/2009 | Sakamoto et al. |
| 2013/0138127 A1 | | 5/2013 | Buckman et al. |

* cited by examiner

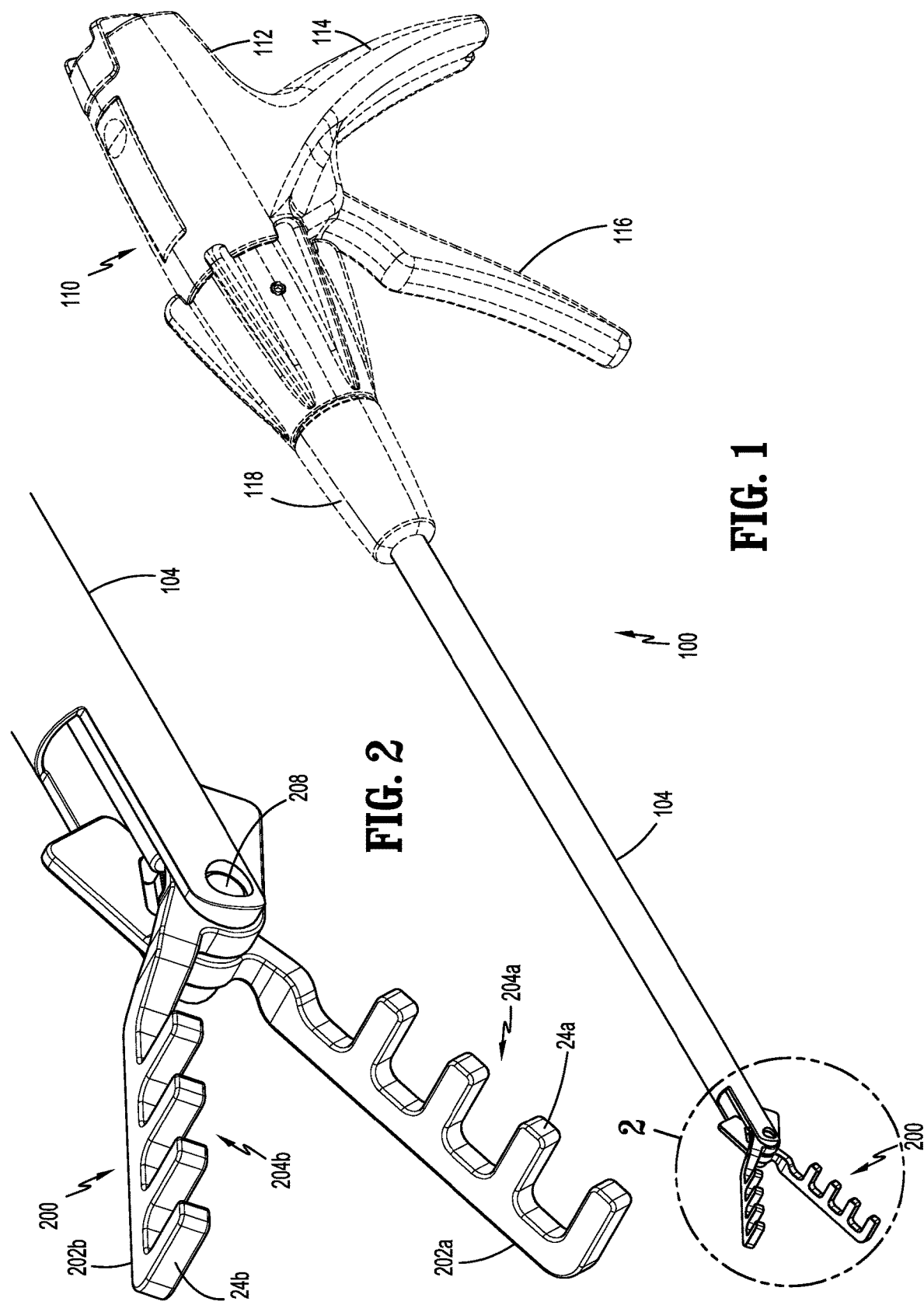

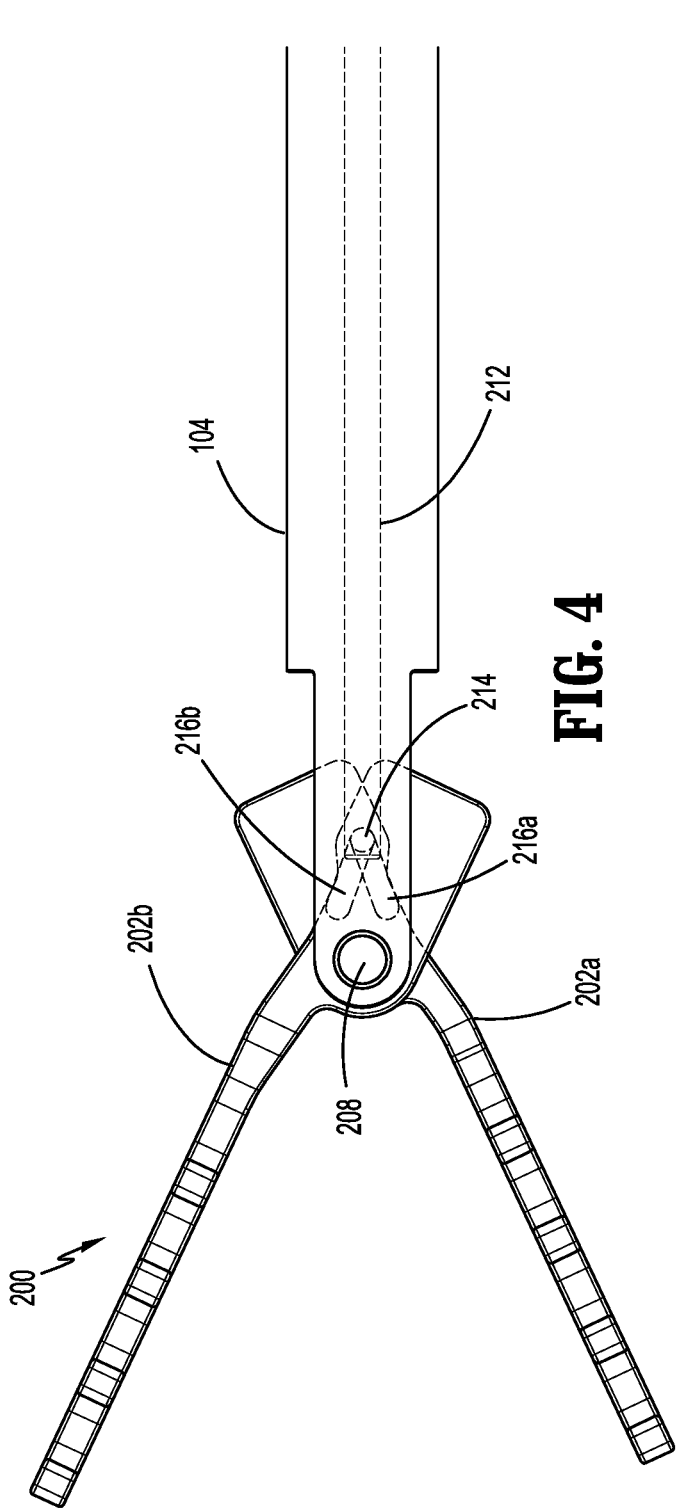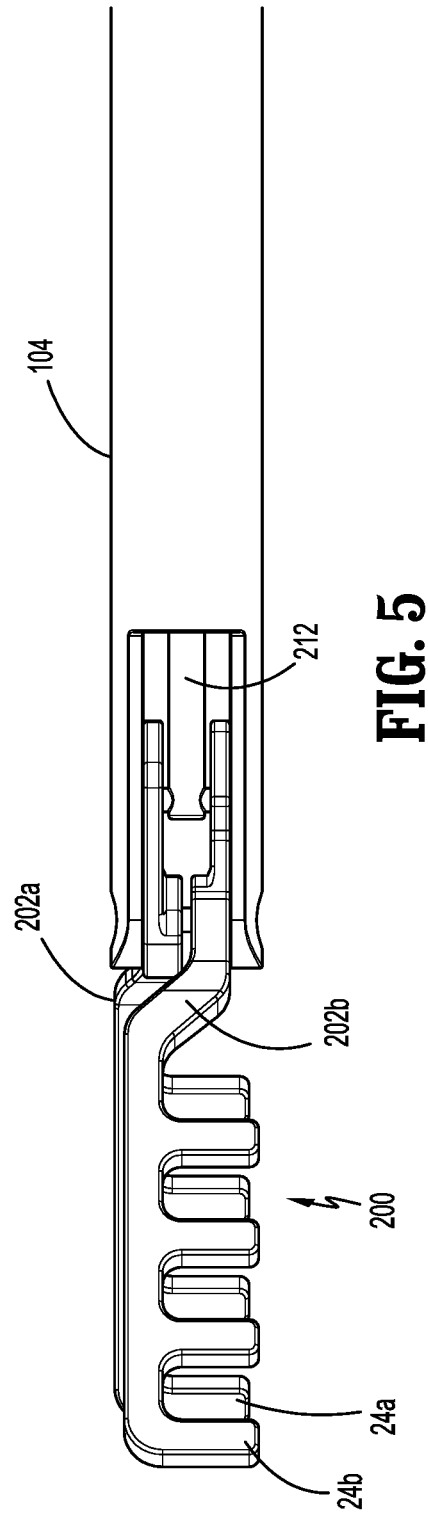

PURSE STRING SUTURE INSTRUMENT

FIELD

The present disclosure is generally related to surgical instruments. More particularly, the present disclosure relates to a purse string suture instrument for placing a purse string during an anastomosis procedure.

BACKGROUND

Anastomosis is the surgical joining of separate hollow organ sections to allow the sections to communicate with each other. Typically, an anastomosis procedure follows surgery in which a diseased or defective section of hollow tissue is removed, and the remaining end sections are to be joined. Depending on the desired anastomosis procedure, the end sections of the hollow organ may be joined using circular, end-to-end, end-to-side, or side-to-side organ reconstruction methods.

In a circular anastomosis procedure, the two ends of the organ sections are joined by means of a surgical stapling instrument which drives a circular array of staples through the organ end sections and cores and removes any overlapping tissue to free a tubular passage. In some applications of a circular anastomosis procedure, an anvil rod having an attached anvil head is mounted to the distal end of a surgical stapling instrument shaft prior to insertion of the instrument into the tissue to be anastomosed. However, in other applications, a detachable anvil rod may be mounted to the instrument subsequent to positioning of the surgical stapling instrument and the anvil assembly within respective tissue sections. In such instances, the surgical stapling instrument and the anvil assembly are separately delivered to the operative site. Each tissue end section is then secured to a respective anvil or staple holding component, e.g., by a purse string suture. The anvil assembly is mounted to the surgical stapling instrument by inserting a mounting portion of the anvil rod within the distal end of the surgical stapling instrument so that a mounting mechanism within the surgical stapling instrument securely engages the anvil rod. Preparation of the tissue sections to be joined and mounting of the anvil rod to the surgical stapling instrument may be performed using minimally invasive surgical techniques, i.e., under laparoscopic guidance.

SUMMARY

The techniques of this disclosure generally relate to an end effector for a surgical device. The end effector includes first and second jaws disposed at a distal portion of an elongate tubular shaft, the first and second jaws pivotably coupled to each other at ends of the first and second jaws that are proximal to the elongate tubular shaft, the first and second jaws spaced apart and defining a gap therebetween. First and second pluralities of teeth extend perpendicularly from the first and second jaws respectively, and the first plurality of teeth is longitudinally offset from the second plurality of teeth. The first and second jaws are transitionable from an open configuration to an approximated configuration. The approximated configuration is adapted to clamp tissue in the gap between the first and second jaws and thereby displacing sections of tissue outwardly between the first and second pluralities of teeth.

In aspects, the ends proximal to the elongate tubular shaft of the first and second jaws of the end effector may be laterally staggered and rotatable in parallel planes, such that in an approximated configuration the first and second jaws are approximately parallel.

In other aspects, the first and second pluralities of teeth may extend in the same direction from their respective jaws and are perpendicular to parallel planes.

In yet another aspect, the first jaw may extend distally farther from the elongate tubular shaft than the second jaw.

In aspects, a proximal portion of the elongate tubular shaft may be adapted to couple with an actuation mechanism.

In another aspect, the actuation mechanism may be configured to transition the first and second jaws between the open and approximated configurations.

In aspects, the teeth of the first plurality of teeth of the first jaw are longitudinally spaced from the teeth of the second plurality of teeth of the second jaw.

A method of suturing tissue includes positioning first and second jaws in an open configuration around tissue to be sutured. The first and second jaws being pivotably coupled to each other and spaced apart defining a gap therebetween. The first and second jaws have respective first and second pluralities of teeth extending perpendicularly therefrom wherein the first plurality of teeth are longitudinally offset from the second plurality of teeth and the first and second jaws extend distally from an elongate tubular shaft. Additionally, the method includes transitioning the first and second jaws from the open configuration to an approximated configuration so as to clamp tissue in the gap between the first and second jaws. The method also includes displacing sections of the clamped tissue outwardly between the first and second pluralities of teeth and then placing a suture through the displaced sections of the clamped tissue. The method also includes releasing the clamped tissue by returning the first and second jaws to the open configuration.

In aspects, transitioning the first and second jaws from the open configuration to the approximated configuration may include laterally staggering the ends of the first and second jaws proximal to the elongate tubular shaft, the ends of the of the first and second jaws also rotatable in parallel planes, such that in the approximated configuration the first and second jaws are approximately parallel.

In other aspects, displacing sections of the clamped tissue outwardly between the first and second pluralities of teeth may include the first and second pluralities of teeth of the first and second jaws extending in the same direction from their respective jaws and perpendicularly to parallel planes.

In yet other aspects, transitioning the first and second jaws from the open configuration to the approximated configuration may include the first jaw extending distally farther from the elongate tubular shaft than the second jaw.

In aspects, the method may include cinching the purse string suture about an anvil of a circular surgical stapler placed inside the section of tissue thereby fixating the anvil inside the section of tissue that was sutured.

The details of one or more aspects of the disclosure are set forth in the accompanying drawings and the description below. Other features, objects, and advantages of the techniques described in this disclosure will be apparent from the description and drawings, and from the claims.

DESCRIPTION OF DRAWINGS

The accompanying drawings, which are incorporated in and constitute a part of this specification, illustrate aspects and features of the disclosure and, together with the detailed description below, serve to further explain the disclosure, in which:

FIG. 1 is a perspective view of a purse string suture instrument including an end effector with first and second jaws;

FIG. 2 is an enlarged view of the area of detail identified in FIG. 1;

FIG. 4 is a top view of the end effector of FIG. 2 with the first and second jaws in an open configuration and an actuation rod shown in phantom;

FIG. 5 is a side view of the end effector of FIG. 2 with the first and second jaws in the open configuration;

Figure 3:
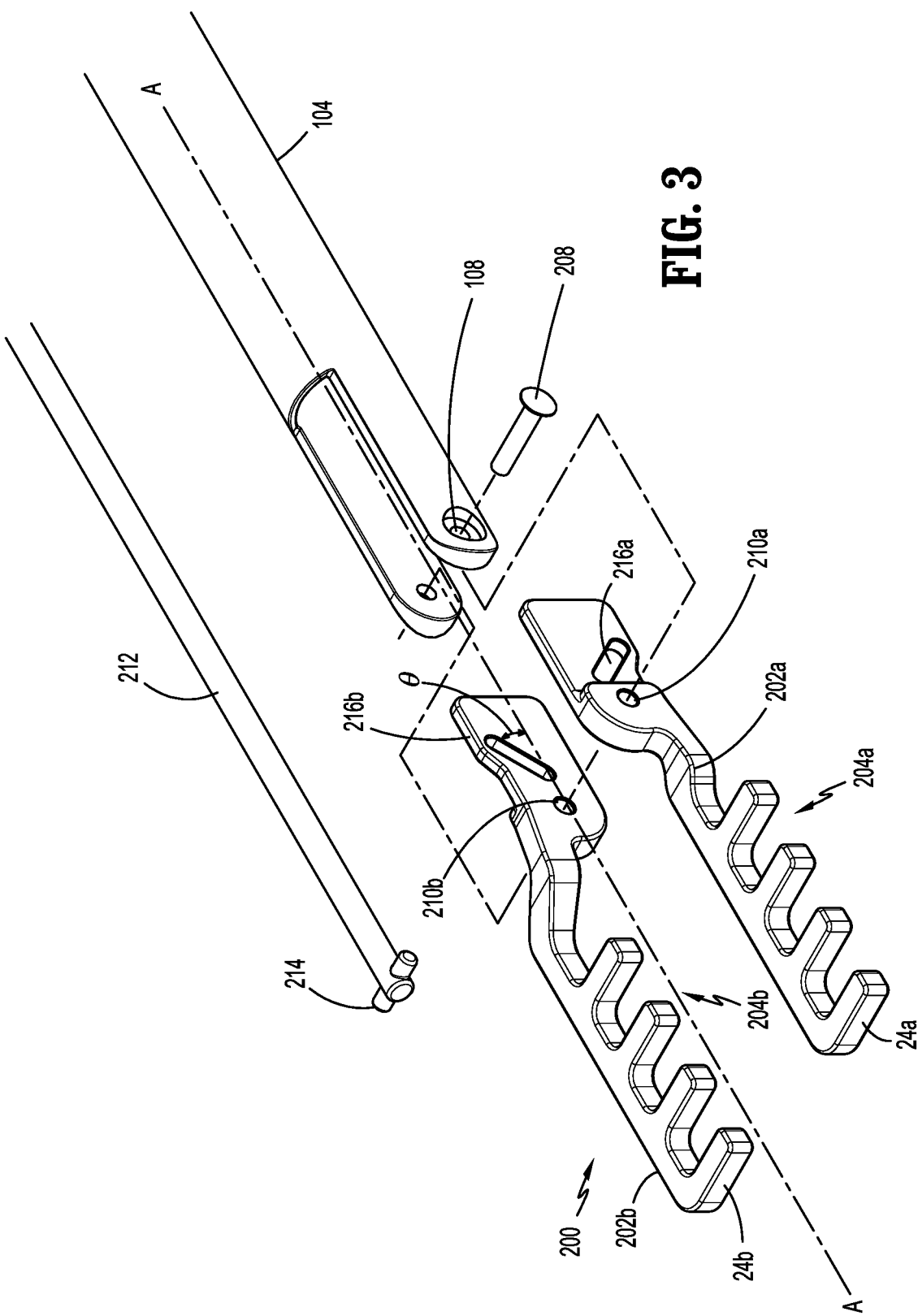
FIG. 3 is an exploded perspective view, with parts separated, of the end effector of FIG. 2.

Further details and various aspects of this disclosure are described in more detail below with reference to the appended figures.

DETAILED DESCRIPTION

Aspects of the presently disclosed purse string suture instrument are described in detail with reference to the drawings, in which like reference numerals designate identical or corresponding elements in each of the several views. However, it is to be understood that the disclosed devices are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an illustrative purse string suture instrument in accordance with the disclosure should typically be considered as available and applicable to other similar features of another device of the disclosure. Accordingly, technical features described herein in connection with one illustrative purse string suture instrument may be applicable to other devices of the disclosure, and thus duplicative descriptions may be omitted herein.

As used herein the term "distal" refers to that portion of the surgical instrument, or component thereof, farther from the user, while the term "proximal" refers to that portion of the surgical instrument, or component thereof, closer to the user.

The term "approximated configuration" refers to a configuration where the jaws of the end effector of the purse string suture instrument are in an approximately parallel configuration so as to clamp a section of tissue.

Referring to FIG. 1, a purse string suture instrument 100 including an end effector 200 with a first jaw 202a, a second jaw 202b, and an actuation mechanism or handle assembly 110 is shown. During anterior resections, it is necessary to place a purse string suture about the periphery of a section of tissue in order to fixate an anvil of a circular stapler, such as an end to end anastomosis stapler (EEA stapler), in a section of colon to make the final staple joint with the EEA stapler similar to that described in U.S. Pat. No. 6,945,444, the entire contents of which are herein incorporated by reference. The end effector 200 is at a distal end of an elongated tubular shaft 104 attached to handle assembly 110 at its proximal end. The handle assembly 110 includes a body 112, a stationary handle 114, a trigger 116, and a collar 118 for coupling the elongated tubular shaft 104 to the handle assembly 110. The end effector 200 is configured to receive and clamp a section of tissue. In aspects, the tissue is a hollow organ tissue. The end effector 200 may be operated manually by pivoting the trigger 116 of the handle assembly 110 towards the stationary handle 114. Alternatively, a robotic actuation mechanism (not shown) may be employed to actuate the end effector 200. In various aspects, the robotic actuation mechanism may be controlled by a surgeon via a computing device in electrical communication with the actuation mechanism. The end effector 200 may be operated by a computing device, server, and/or network (not shown), which may include memory, storage device(s), controllers (e.g. software) for operating the end effector.

Figure 6:
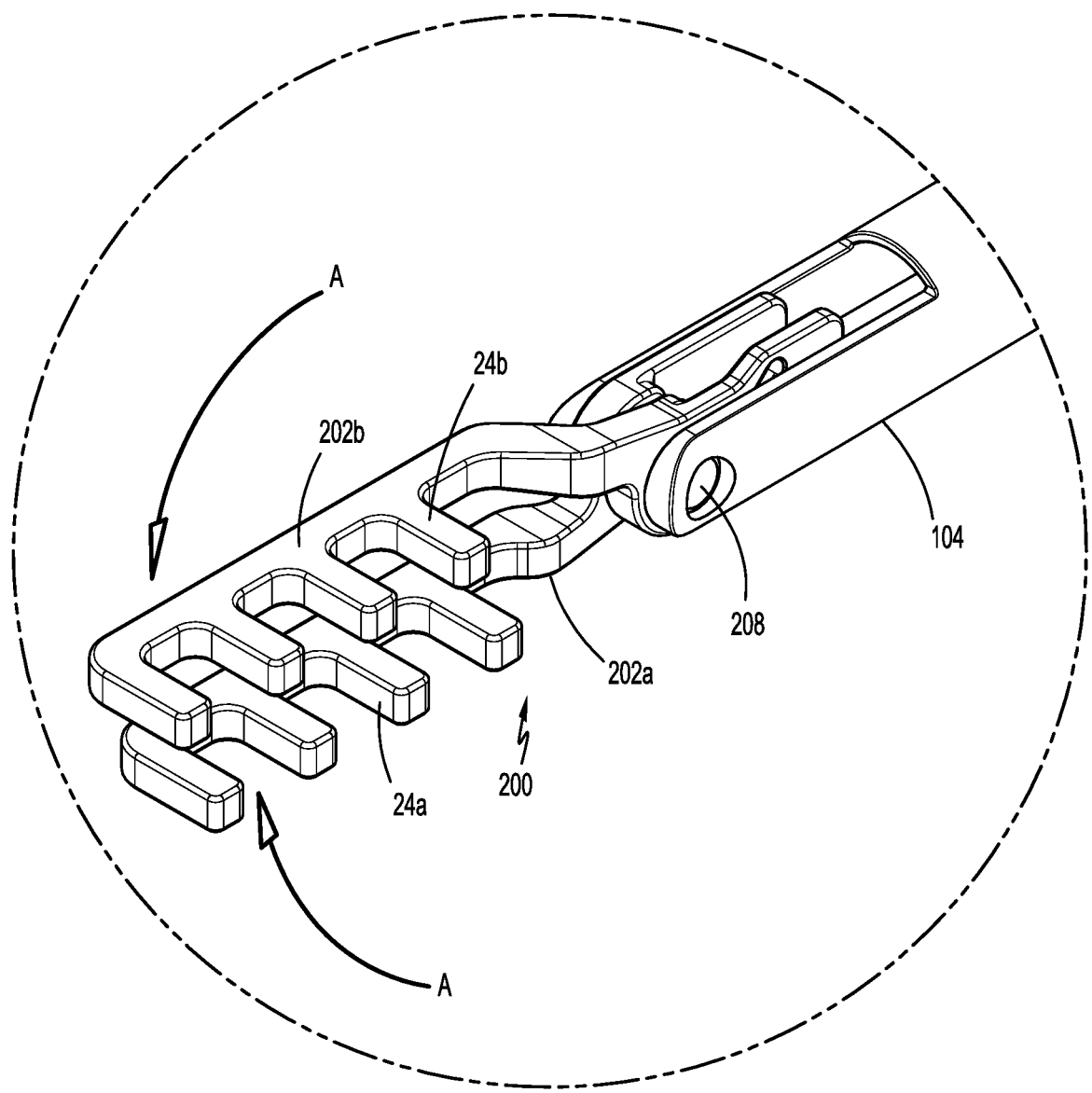
FIG. 6 is a perspective view of the end effector of FIG. 2 with the first and second jaws in an approximated configuration.

Referring additionally to FIG. 2, the end effector 200 with first and second jaws 202a, 202b is shown in further detail. The first jaw 202a and the second jaw 202b are connected at their proximal ends and connected to a distal end of the elongate tubular shaft 104. The first and second jaws 202a, 202b are pivotably coupled to each other at their proximal ends via a pin 208. The first and second jaws 202a, 202b are spaced apart so as to define a gap therebetween sufficiently large enough to clamp a desired section of tissue between the first and second jaws 202a, 202b. The first and second jaws 202a, 202b are movable between an open configuration and an approximated configuration (FIG. 6). The handle assembly 110 (shown in FIG. 1) controls the position of the first and second jaws 202a, 202b allowing a user to transition the end effector 200 from the open configuration to the approximated configuration and vice versa. The first jaw 202a may extend farther in a distal direction than the second jaw 202b from the elongate tubular shaft 104 as seen in FIG. 5. The first jaw 202a and the second jaw 202b include first and second pluralities of teeth 204a, 204b, respectively. The first plurality of teeth 204a includes teeth 24a and the second plurality of teeth 204b includes teeth 24b. The first jaw 202a may extend farther in a distal direction than the second jaw 202b such that the first plurality of teeth 204a is longitudinally offset from the second plurality of teeth 204b as seen in FIG. 5. The first and second jaws 202a, 202b may be laterally staggered and rotatable in parallel planes. In aspects, the first and second jaws 202a, 202b are rotatable such that in an approximated configuration the first and second jaws 202a, 202b are approximately parallel as shown in FIG. 6.

With reference to FIG. 3, a perspective view of the end effector 200 with its various components separated is shown. First and second jaws 202a, 202b are pivotably connected to the end of elongate tubular shaft 104 by the pin 208 inserted through holes 210a, 210b at proximal ends of the first and second jaws 202a, 202b and openings 108 in the elongated tubular shaft 104. An actuation rod 212 includes opposed protrusions 214 that are positioned in first and second slots 216a, 216b that are located in proximal regions of the first and second jaws 202a, 202b, respectively, for transitioning the configuration of the first and second jaws 202a, 202b between the open configuration and the approximated configuration. First and second slots 216a, 216b may be positioned at acute angles relative to a longitudinal axis A-A of the first and second jaws 202a, 202b and the elongated tubular shaft 104, in reverse reflections of each other, such that, when the first and second jaws 202a, 202b are in the approximated configuration, the first and second slots 216a, 216b define an acute angle θ when viewed from the side. The protrusions 214 of the actuation rod 212 are positioned in the slots 216a, 216b, such that, when the actuation rod 212 is translated in a distal direction, it slides the protrusions 214 distally in the slots 216a, 216b so as to transition the first and second jaws 202a, 202b from the open configuration to the approximated configuration. As the actuation rod 212 moves proximally, the protrusions 214 slide in the first and second slots 216a, 216b so as to transition the first and second jaws 202a, 202b to the open configuration from the approximated configuration. In aspects, the first and second jaws 202a, 202b may be actuated by a variety of mechanisms, as known in the art, for transitioning the first and second jaws 202a, 202b between an open configuration and a approximated configuration. For example, the first and second jaws 202a, 202b may be actuated by individual motors coupled to proximal ends of the first and second jaws 202a, 202b. The actuation rod 212 may be displaced between its proximal position and its distal position using the trigger 116 of the handle assembly 110 (see FIG. 1). The second jaw 202b may be constructed so that the first and second jaws 202a, 202b, when in the approximated position, align longitudinally on approximately the same plane.

Referring to FIGS. 4 and 5, the end effector 200 is shown in the open configuration in a top and side view, respectively. In the open configuration the first and second jaws 202a, 202b are sufficiently spaced apart so as to accept a section of tissue to be clamped and sutured. The actuation rod 212 is shown in phantom in FIG. 4 in a proximal position. The protrusions 214 of the actuation rod 212 are positioned in proximal ends of the first and second slots 216a, 216b, thereby maintaining the first and second jaws 202a, 202b in the open configuration. Pin 208 is shown coupling the first and second jaws 202a, 202b to each other at a distal end of the elongate tubular shaft 104. In aspects, the first and second jaws may be pivotable from about zero degrees (0) to about one hundred and eighty degrees (180) about pin 208. In the open configuration, first and second jaws 202a, 202b may define an acute angle.

Figure 7:
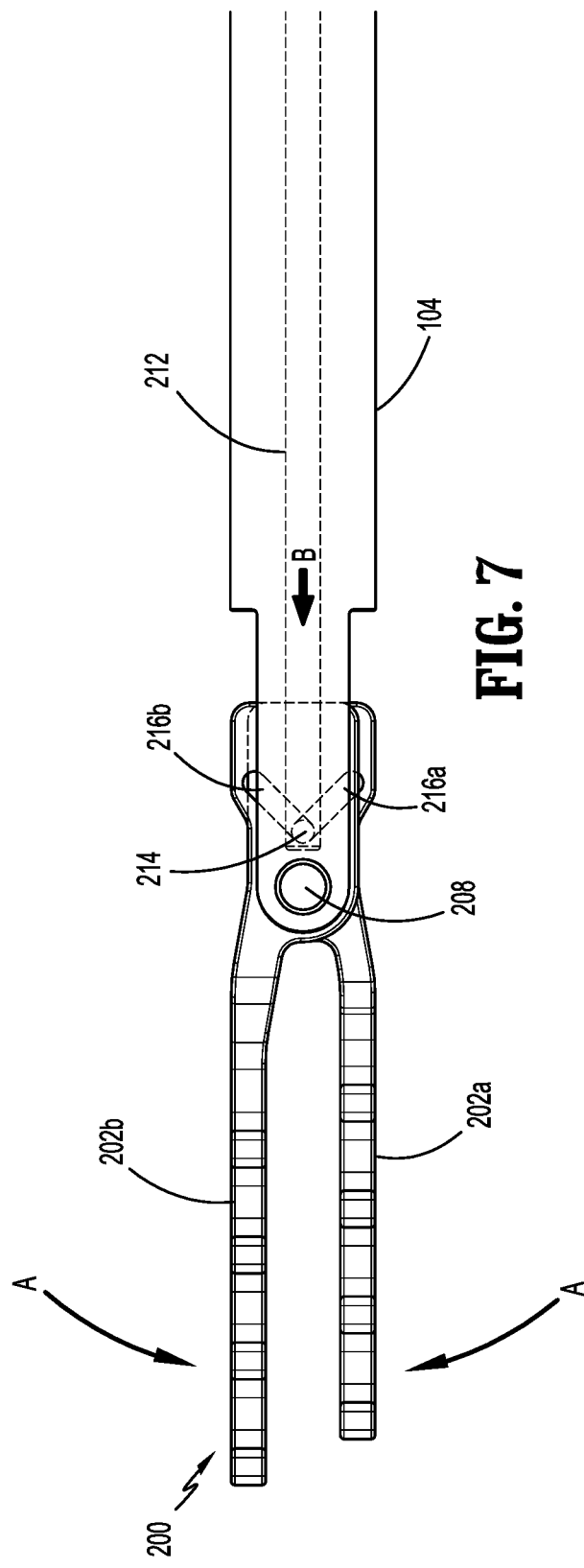
FIG. 7 is a top view of the end effector of FIG. 2 with the first and second jaws in the approximated configuration and the actuation rod shown in phantom.
Figure 8:
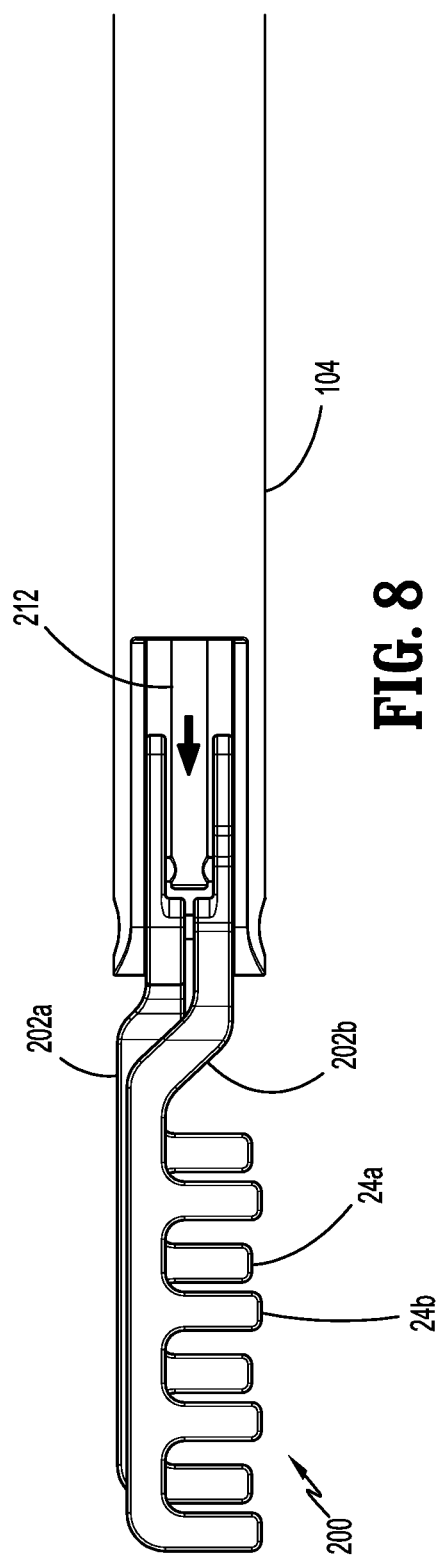
FIG. 8 is a side view of the end effector of FIG. 2 with the first and second jaws in the approximated position.
Figure 10:
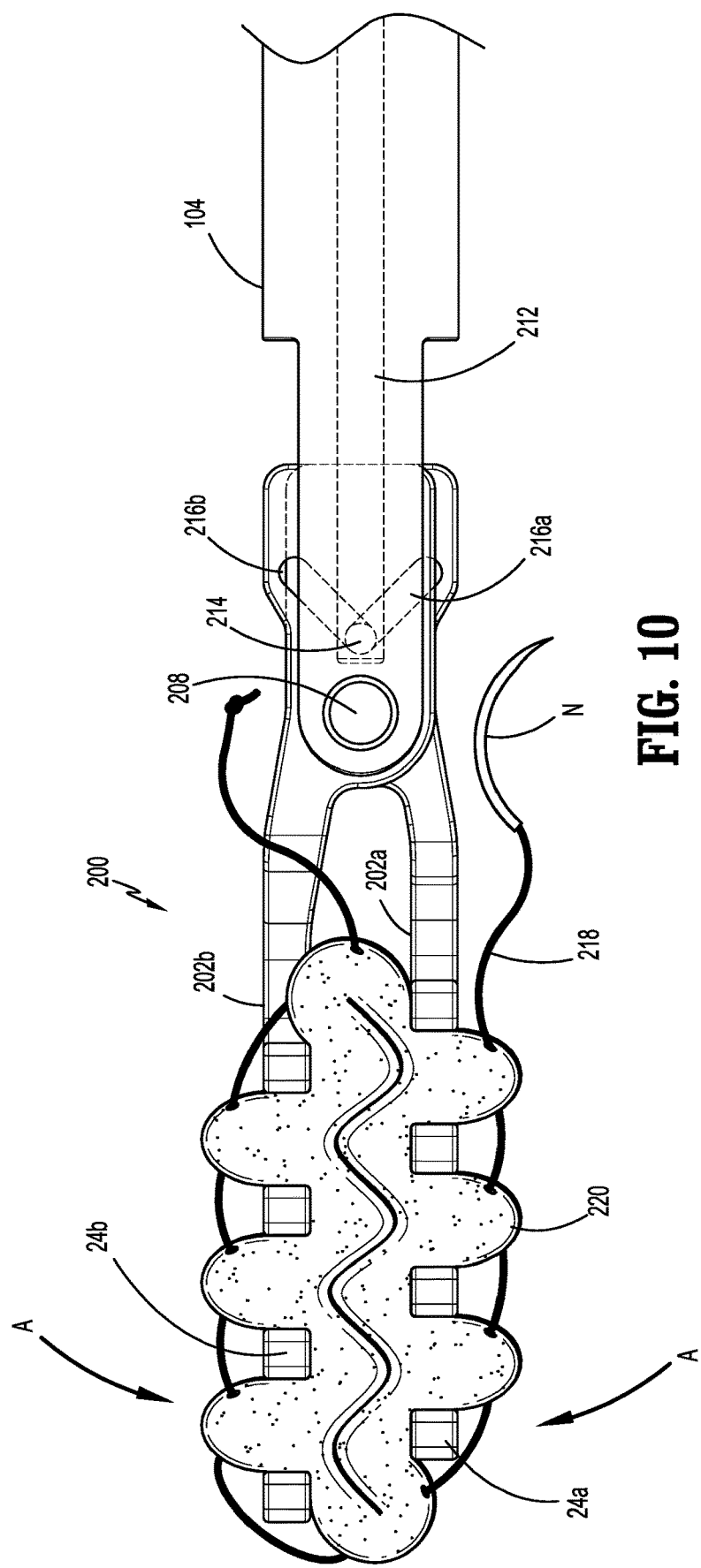
FIG. 10 is a top view of the end effector of FIG. 9 in the approximated configuration clamping a section of tissue and a purse string suture.

Referring to FIGS. 6, 7, and 8, the end effector 200 is shown in the approximated configuration in perspective, top, and side views, respectively. Proximal ends of the first and second jaws 202a, 202b are laterally staggered and rotatable in parallel planes such that in the approximated configuration the first and second jaws 202a, 202b are approximately parallel. The first and second pluralities of teeth 204a, 204b of the first and second jaws 202a, 202b extend in the same direction from their respective jaws and are perpendicular to parallel planes when the end effector 200 is in the approximated configuration (FIG. 7). As shown in FIGS. 7 and 8, the second jaw 202b may extend farther in a distal direction than the first jaw 202a from the elongate tubular shaft 104. In aspects, the first jaw 202a may extend farther in a distal direction than the second jaw 202b from the elongate tubular shaft 104. Actuation rod 212 is moved distally in the direction of arrow "B", sliding the protrusions 214 distally in slots 216a, 216b thereby causing the first and second jaws 202a, 202b to rotate in the direction of arrows "A" and into the approximated configuration (FIGS. 6 and 7). When the first and second jaws 202a, 202b are transitioned from the open configuration to the approximated configuration, the first and second jaws 202a, 202b clamp a section of tissue positioned between the first and second jaws 202a, 202b while the jaws were in the open configuration. Portions of the clamped tissue are displaced between the pluralities of teeth 204a, 204b when the end effector 200 is in the approximated configuration (FIG. 10). The first jaw 202a may extend farther in a distal direction than the second jaw 202b such that each tooth 24a of the first plurality of teeth 204a is longitudinally offset from each tooth 24b of the second plurality of teeth 204b, thereby maximizing the amount of tissue displaced between the first and second pluralities of teeth 204a, 204b. In aspects, either the first or second jaw 202a, 202b may extend farther in a distal direction so as to offset the first and second pluralities of teeth 204a, 204b to maximize tissue displacement when the end effector 200 is in the approximated configuration. In other aspects, the first and second jaws 202a, 202b may extend an equal distance in a distal direction from the elongate tubular shaft 104, and the first and second pluralities of teeth 204a, 204b may be staggered along their respective first and second jaws 202a, 202b, such that one of the first or second pluralities of teeth 204a, 204b is offset from the other of the first or second pluralities of teeth 204a, 204b in order to maximize tissue displacement. By displacing maximal amounts of the clamped section of tissue, a purse string suture 218 can be readily threaded through the tissue displaced between the first and second pluralities of teeth 204a, 204b (see FIG. 10). The first and second pluralities of teeth 204a, 204b may be variably offset longitudinally so as to maximize displacement of different types and/or sizes of tissues to be sutured. In aspects, any number of teeth 24a, 24b may be disposed on the first and second jaws 202a, 202b so as to form the first and second pluralities of teeth 204a, 204b. For example, the first plurality of teeth 204a may include four (4) teeth 24a sufficiently spaced apart so as to allow a sufficient section of colon to be displaced between the plurality of first teeth 204a to allow a suture to be run through the periphery of the tissue. The opposing second plurality of teeth 204b may include five (5) teeth 24b offset from the four (4) teeth 24a of the first plurality of teeth 204a in the example, also sufficiently spaced apart so as to allow sections of colon to be displaced between the first and second pluralities of teeth 204a, 204b, so as to place the purse string suture 218 about the entire periphery of displaced tissue through the end effector 200. Any suitable number of teeth 24a, 24b may be included in each of the first and second pluralities of teeth 204a, 204b for maximizing the amount of tissue displaced. The distance between each tooth 24a, 24b on the same jaw of the first and second pluralities of teeth 204a, 204b may be uniform or different. The distance between each tooth 24a, 24b on the same jaw of the first and second pluralities of teeth 204a, 204b may be sufficiently spaced apart such that a sufficient amount of tissue is displaced such that there is sufficient tissue to be sutured without tearing the tissue and/or there is sufficient tissue to hold the suture in place.

Figure 9:
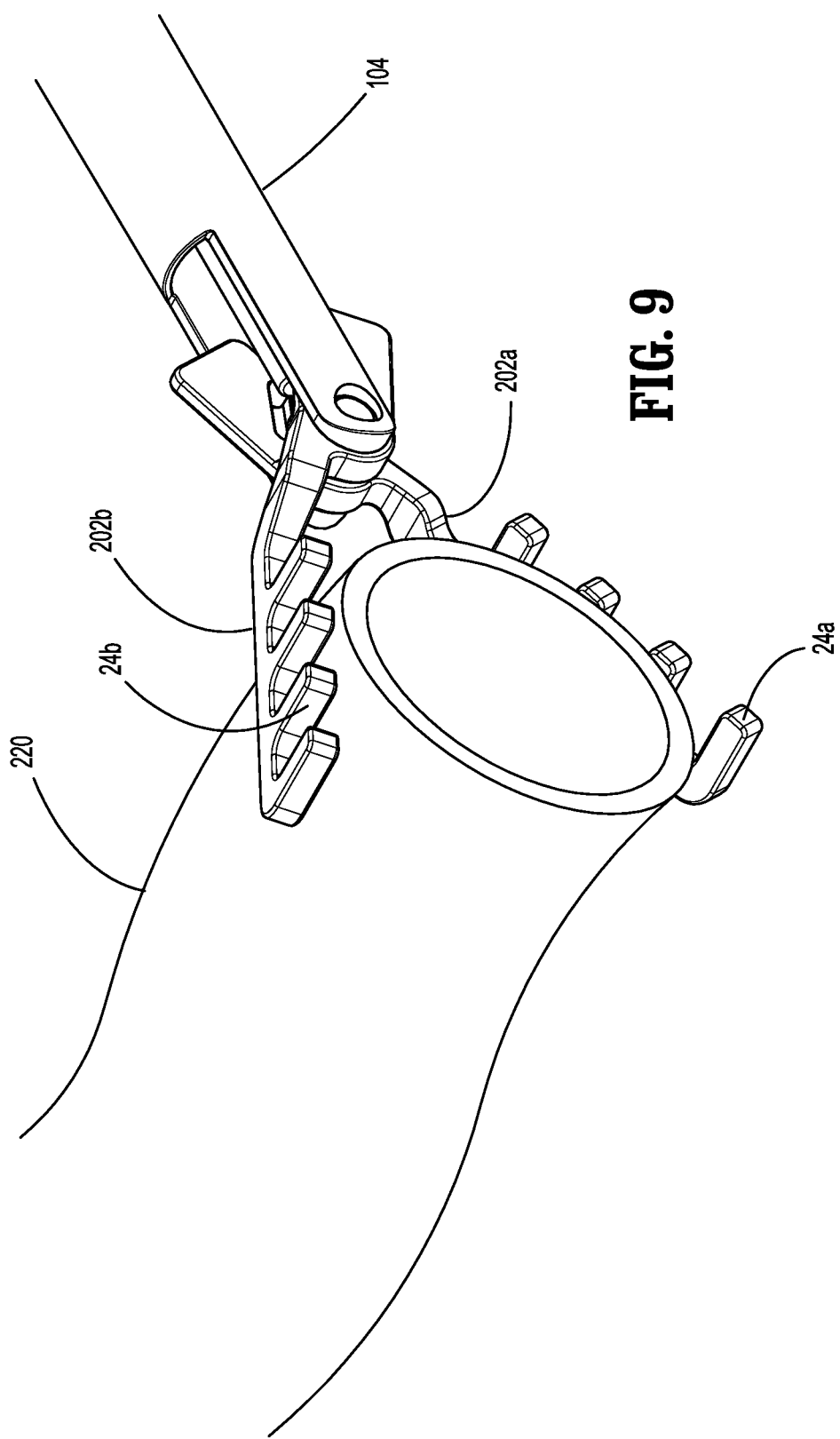
FIG. 9 is a perspective view of the end effector of FIG. 2 with the first and second jaws in the open configuration and positioned about a section of tissue to be sutured.

Referring to FIGS. 9 and 10, the purse string suture instrument 100 of this disclosure is operatively shown in the open configuration about a section of tissue 220 and in the approximated configuration clamping the section of tissue 220, respectively. The section of tissue 220 to be sutured is positioned between the first and second jaws 202a, 202b in the open configuration (FIG. 9). Actuating the trigger 116 of the handle assembly 110 (FIG. 1) moves the actuation rod 212 distally so as to transition the first and second jaws 202a, 202b to the approximated configuration (FIG. 10). As the first and second jaws 202a, 202b approach each other, the tissue 220 is clamped and displaced outward between gaps in the longitudinally offset first and second pluralities of teeth 204a, 204b. Once the tissue 220 is clamped and portions of the tissue 220 sufficiently displaced outward between the first and second pluralities of teeth 204a, 204b, a purse string suture 218 with a needle N may be placed through the displaced portions of the tissue 220 (FIG. 10). In particular, displaced portions of tissue 220 extend through the first and second jaws 202a, 202b in a staggered arrangement. Sections of tissue 220 extending through the teeth 24a of the first plurality of teeth 204a of the first jaw 202a are longitudinally offset from sections of tissue 220 extending through the teeth 24b of the second plurality of teeth 204b of the second jaw 202b. After the purse string suture 218 is placed through the tissue 220, the actuation rod 212 is moved to a proximal position, transitioning the end effector 200 from the approximated configuration (FIG. 10) to the open configuration (FIG. 9), thereby releasing the clamped and sutured tissue 220. The end effector 200 is then removed from around the section of tissue 220 so that a surgeon may continue a surgical procedure.

Figure 11:
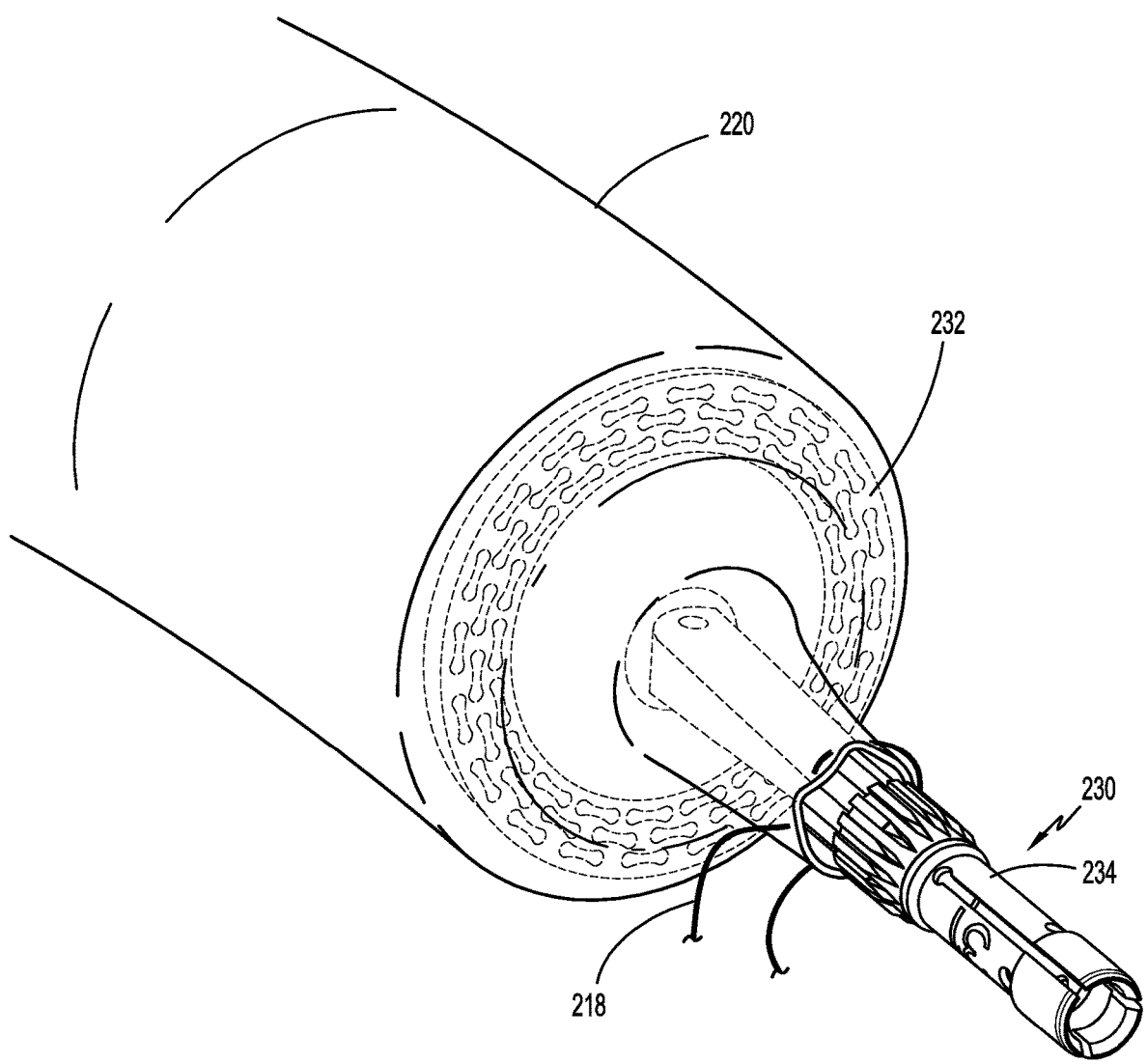
FIG. 11 is an end perspective view of a tubular organ with a purse string suture applied thereto and an anvil assembly shown partially in phantom.

With reference to FIG. 11, the purse string suture 218 is cinched about the anvil shaft 234 of an EEA stapler, so the EEA stapler may be used to create an anastomosis. The anvil shaft 234 is part of an anvil assembly 230 that also includes an anvil 232. The anastomosis creates a passage between two sections of tissue, and the anvil 232 allows the EEA stapler to make that connection possible. Before the anvil 232 is positioned by the surgeon in the section of tissue 220 to be used for the anastomosis, the purse string suture 218 is threaded about the periphery of the hollow organ tissue 220. The end effector 200 (FIG. 1) facilitates placement of the purse string suture 218 by clamping the section of tissue 220 to be fixated around the anvil 232 of the EEA stapler, displacing as much of the tissue 220 as desired through first and second pluralities of teeth 204a, 204b (FIG. 10) disposed on the first and second jaws 202a, 202b of the end effector 200, and then threading the purse string suture 218 and needle N through the displaced tissue 220. The method for placing the purse string suture 218 includes first positioning the end effector 200 in an open configuration about a section of tissue 220 (FIG. 9), and then actuation rod 212 is moved to a distal position causing protrusions 214 to slide distally in slots 216a, 216b thereby transitioning the end effector 200 from the open configuration to the approximated configuration. At the next step, the tissue 220 is clamped by the first and second jaws 202a, 202b of the end effector 200 in the approximated configuration, and portions of the tissue 220 are displaced through the longitudinally staggered first and second pluralities of teeth 204a, 204b on the first and second jaws 202a, 202b of the end effector 200. Thereafter, the purse string suture 218 is threaded through the periphery of displaced portions of tissue 220. After the purse string suture 218 is placed, the actuation rod 212 is moved to a proximal position, transitioning the first and second jaws 202a, 202b of the end effector 200 from the approximated configuration to the open configuration thereby releasing the clamped section of tissue 220, and the end effector then removed from the tissue 220. The anvil 232 of an EEA stapler may be situated inside the section of tissue 220 before the purse string suture 218 is placed, or it may be inserted after the purse string suture 218 is threaded through the displaced tissue 220. In the former situation, before the end effector 200 is positioned about a section of tissue 220, the anvil 232 is positioned away from the first and second jaws 202a, 202b so as not to interfere with the end effector 200. In either situation, after the purse string suture 218 is placed and the end effector is removed, the anvil 232 may be moved into position such that the purse string suture 218 can be cinched around the anvil shaft 234 of the EEA stapler in order to hold it in place, as shown in FIG. 11, enabling the EEA stapler to readily engage the anvil 232 to create the anastomosis. The last step includes cinching the purse string suture 218 about the anvil shaft 234 and adjusting the purse string suture as desired, after which the surgeon may engage the anvil with the EEA stapler to create an anastomosis.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An end effector for a surgical device comprising:
first and second jaws disposed at a distal portion of an elongate tubular shaft, the first and second jaws pivotably coupled to each other at ends of the first and second jaws that are proximal to the elongate tubular shaft, the first and second jaws spaced apart and defining a gap therebetween; and
first and second pluralities of teeth extending perpendicularly in the same direction from the first and second jaws respectively, the first plurality of teeth longitudinally offset from the second plurality of teeth;
wherein the first and second jaws are transitionable from an open configuration to an approximated configuration, the approximated configuration adapted to clamp tissue in the gap between the first and second jaws and thereby displacing sections of tissue outwardly between the first and second pluralities of teeth.

2. The end effector of claim 1, wherein the ends proximal to the elongate tubular shaft of the first and second jaws are laterally staggered and rotatable in parallel planes, such that in an approximated configuration the first and second jaws are approximately parallel.

3. The end effector of claim 2, wherein the first and second pluralities of teeth extend perpendicular to parallel planes.

4. The end effector of claim 1, wherein the first jaw extends distally farther from the elongate tubular shaft than the second jaw.

5. The end effector of claim 1, wherein a proximal portion of the elongate tubular shaft is adapted to couple with an actuation mechanism.

6. The end effector of claim 5, wherein the actuation mechanism is configured to transition the first and second jaws between the open and approximated configurations.

7. The end effector of claim 1, wherein the teeth of the first plurality of teeth of the first jaw are longitudinally spaced from the teeth of the second plurality of teeth of the second jaw.

8. An end effector for a surgical device comprising:
first and second jaws disposed at a distal portion of an elongate tubular shaft, the first and second jaws pivotably coupled to each other at ends of the first and second jaws that are proximal to the elongate tubular shaft, the first and second jaws spaced apart and defining a gap therebetween, the ends proximal to the elongate tubular shaft of the first and second jaws laterally staggered and rotatable in parallel planes; and
first and second pluralities of teeth extending perpendicularly from the first and second jaws respectively, the first plurality of teeth longitudinally offset from the second plurality of teeth;
wherein the first and second jaws are transitionable from an open configuration to an approximated configuration, when in the approximated configuration, the first and second jaws are approximately parallel, the approximated configuration adapted to clamp tissue in the gap between the first and second jaws and thereby displacing sections of tissue outwardly between the first and second pluralities of teeth.

9. The end effector of claim 8, wherein the first jaw extends distally farther from the elongate tubular shaft than the second jaw.

10. The end effector of claim 8, wherein a proximal portion of the elongate tubular shaft is adapted to couple with an actuation mechanism.

11. The end effector of claim 10, wherein the actuation mechanism is configured to transition the first and second jaws between the open and approximated configurations.

12. The end effector of claim 8, wherein the teeth of the first plurality of teeth of the first jaw are longitudinally spaced from the teeth of the second plurality of teeth of the second jaw.

* * * * *